(12) United States Patent
Barolet et al.

(10) Patent No.: US 6,782,161 B2
(45) Date of Patent: Aug. 24, 2004

(54) LASER DIODE APPARATUS PROVIDED WITH AN AIMING BEAM AND INJECTION METHOD THEREFOR

(75) Inventors: Daniel Barolet, Laval (CA); Jean-François Cormier, St-Augustin-de-Desmaures (CA); Philippe Gagnon, Sainte-Foy (CA); Marc-André Boucher, Lac-Beauport (CA); Jacques Godin, Val-Bélair (CA); Pascal Bourqui, Sainte-Foy (CA); Deni Bonnier, Lévis (CA); Michel Doucet, Sainte-Foy (CA)

(73) Assignee: Derma Laser Inc., Quebec (CA)

( * ) Notice: Subject to any disclaimer, the term of this patent is extended or adjusted under 35 U.S.C. 154(b) by 286 days.

(21) Appl. No.: 09/777,873

(22) Filed: Feb. 7, 2001

(65) Prior Publication Data

US 2002/0106152 A1 Aug. 8, 2002

(51) Int. Cl.$^7$ ................................................. G02B 6/32
(52) U.S. Cl. .............................. 385/33; 385/27; 385/39
(58) Field of Search ........................... 385/33, 124, 39, 385/45, 27, 31

(56) References Cited

U.S. PATENT DOCUMENTS

| 4,307,934 | A | * | 12/1981 | Palmer ....................... 350/96.2 |
| 4,575,181 | A | * | 3/1986 | Ishikawa ..................... 350/96.2 |
| 4,625,333 | A | * | 11/1986 | Takezawa et al. ............ 455/612 |
| 4,761,054 | A | | 8/1988 | Ishimori et al. ............ 350/96.26 |
| 5,123,845 | A | | 6/1992 | Vassiliadis et al. ........... 433/214 |
| 5,353,294 | A | * | 10/1994 | Shigeno ......................... 372/43 |
| 5,526,455 | A | * | 6/1996 | Akita et al. ..................... 385/93 |
| 5,630,811 | A | | 5/1997 | Miller ............................. 606/9 |
| 5,631,992 | A | * | 5/1997 | Takahashi et al. .............. 385/94 |
| 5,787,215 | A | * | 7/1998 | Kuhara et al. ................. 385/88 |
| 6,031,850 | A | | 2/2000 | Cheo .............................. 372/6 |
| 6,072,814 | A | | 6/2000 | Ryan et al. .................... 372/35 |
| 6,144,787 | A | | 11/2000 | Johnston et al. ............... 385/31 |
| 6,304,695 | B1 | * | 10/2001 | Shekel .......................... 385/33 |
| 6,349,159 | B1 | * | 2/2002 | Uebbing et al. ............... 385/33 |
| 6,419,405 | B1 | * | 7/2002 | Boscha ......................... 385/93 |

FOREIGN PATENT DOCUMENTS

JP 11312833 A 11/1999

OTHER PUBLICATIONS

International Search Report listing the above references for corresponding international application PCT/CA02/00071 completed on Apr. 2, 2002 (3pgs.). Authorized Officer: Riblet, P.

* cited by examiner

*Primary Examiner*—Phan T. H. Palmer
(74) *Attorney, Agent, or Firm*—Lorusso Loud & Kelly LLP; Marc Lupien

(57) ABSTRACT

A laser apparatus provided with an aiming beam using a method for the injection of both laser light and aiming beam forming light in an optic fiber will be described herein. More specifically, the present disclosure describes a method, an injection module and a laser apparatus designed to inject laser light into the core and aiming beam forming light into the cladding of the optic fiber.

20 Claims, 7 Drawing Sheets

FIG-5

LASER DIODE APPARATUS PROVIDED WITH AN AIMING BEAM AND INJECTION METHOD THEREFOR

FIELD OF THE INVENTION

The present invention generally relates to laser apparatuses. More specifically, the present invention is concerned with a laser diode apparatus provided with an aiming beam and with a method for the injection of laser light and of aiming beam forming light, for example, non-coherent light, in an optic fibre therefor.

BACKGROUND OF THE INVENTION

Over the years, laser diode apparatuses have demonstrated their usefulness in many tasks such as, for example, for hair removal, dermatology treatment and endoscopic laser surgery.

In the case of hair removal, the laser diode technology is generally considered by dermatologists as one of the most efficient permanent hair removal techniques.

Various laser apparatuses and methods for hair removal have been disclosed in the prior art. For example, U.S. Pat. No. 5,630,811, issued to Miller and entitled "Method and apparatus for hair removal", generally discloses a method and an apparatus that may be used for hair removal using a modified fibre optically delivered laser source.

A drawback with Miller apparatus is the use of a cooling tube which makes the handpiece bulky and more difficult to use. Furthermore, aiming the laser energy to the correct location may be problematic since it includes a distinct fibre optic delivery system.

Various systems have been proposed to provide easier aiming of the laser beam emitted by a laser apparatus. For example, U.S. Pat. No. 5,123,845, entitled: "Dental laser assembly" and issued to Vassiliadis et al., describes such an apparatus where a second aiming beam is introduced in the core of the fibre transporting the laser beam. A drawback with Vassiliadis system is related to the use of flash lamp pumped solid state lasers which are less efficient. The system is also complicated by the injection of the aiming beam in the transport fibre through the solid state laser itself, thus requiring careful alignment of both lasers and the fibre on the same axis.

SUMMARY OF THE INVENTION

More specifically, in accordance with the present invention, there is provided an injection module for injecting laser light and aiming beam forming light into an optic fibre having a core and a cladding; the injection module comprising:

a first radiation source emitting laser light;
a second radiation source emitting aiming beam forming light; and
a lens arrangement so configured as to a) collimate and focus the emitted laser light into the core of the optic fibre, and b) establish the propagation of the aiming beam forming light into the cladding of the optic fibre.

According to another aspect of the present invention, there is provided a laser diode apparatus comprising:

an optic fibre having a core and a cladding; the optic fibre having a proximate and a distal end;
an injection module for injecting laser light and aiming beam forming light into the proximate end of the optic fibre; the injection module including:
a first radiation source emitting laser light;
a second radiation source emitting aiming beam forming light; and
a lens arrangement so configured as to a) collimate and focus the emitted laser light into the core of the optic fibre, and b) establish the propagation of the aiming beam forming light into the cladding of the optic fibre; and
a handheld module mounted to the distal end of the optic fibre.

According to a third aspect of the present invention, there is provided a method for injecting laser light and aiming beam forming light into an optic fibre having a core and a cladding; the method comprising the steps of:

providing a source of laser light;
providing a source of aiming beam forming light;
collimating and focusing the laser light emitted by the source of laser light into the core of the optic fibre; and
establishing the propagation of the aiming beam forming light emitted by the source of aiming beam forming light into the cladding of the optic fibre.

Other objects, advantages and features of the present invention will become more apparent upon reading of the following nonrestrictive description of preferred embodiments thereof, given by way of example only with reference to the accompanying drawings.

DESCRIPTION OF THE PREFERRED EMBODIMENT

Figure 1:
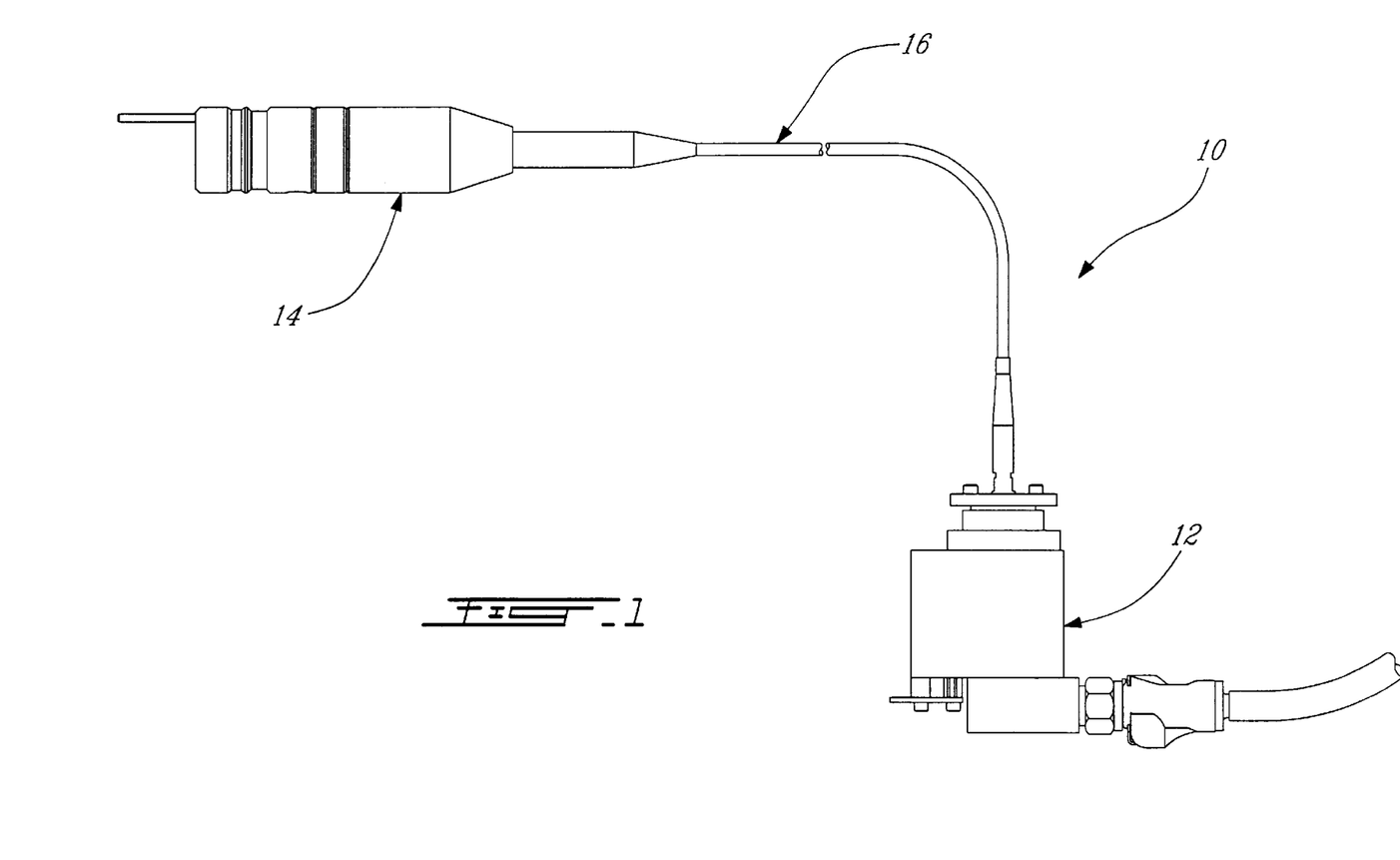
FIG. 1 is a side elevational view of a diode laser apparatus according to an embodiment of the present invention.

Turning now to FIG. 1 of the appended drawings, a laser diode apparatus 10 according to an embodiment of the present invention will be described. The apparatus 10 is designed for hair removal.

The apparatus 10 includes an injection module 12, a handheld module 14 and a single optic fibre 16 linking both modules 12 and 14.

Figure 2:
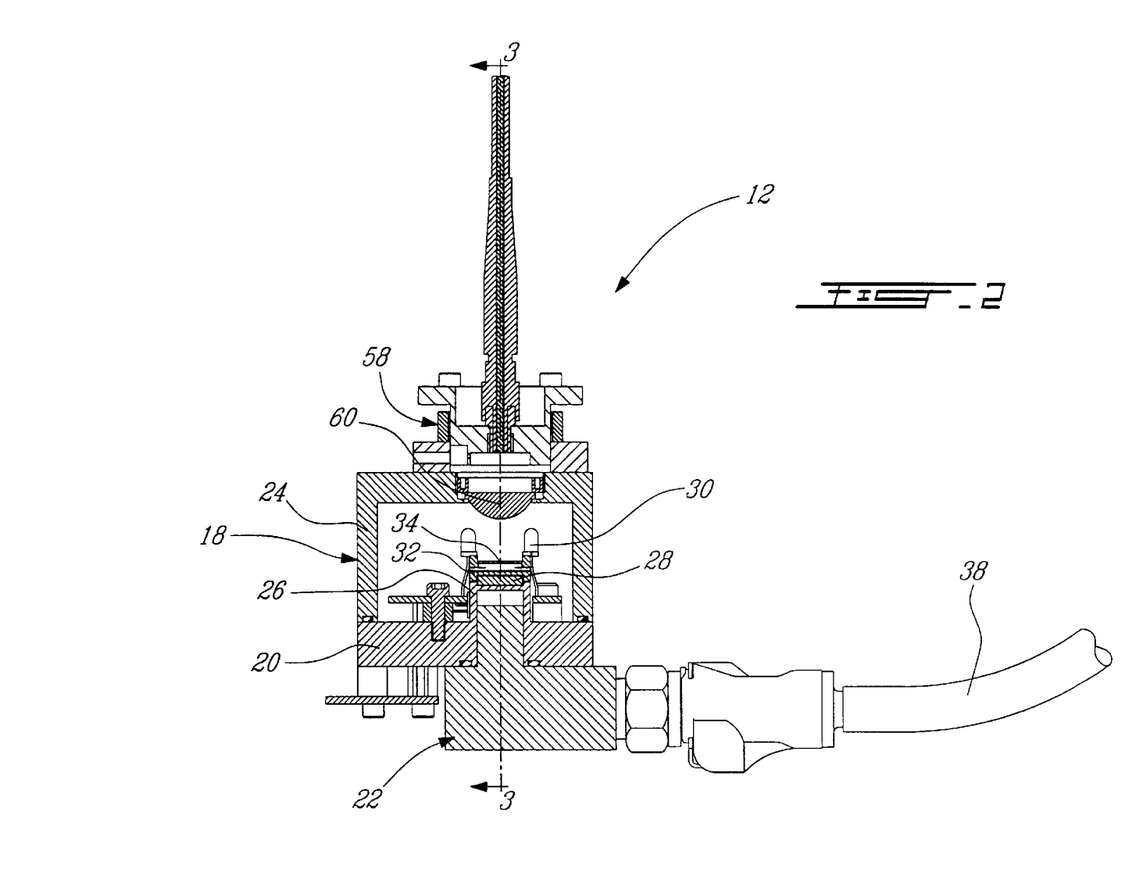
FIG. 2 is a side elevational sectional view of the injection module of the apparatus of FIG. 1.
Figure 3:
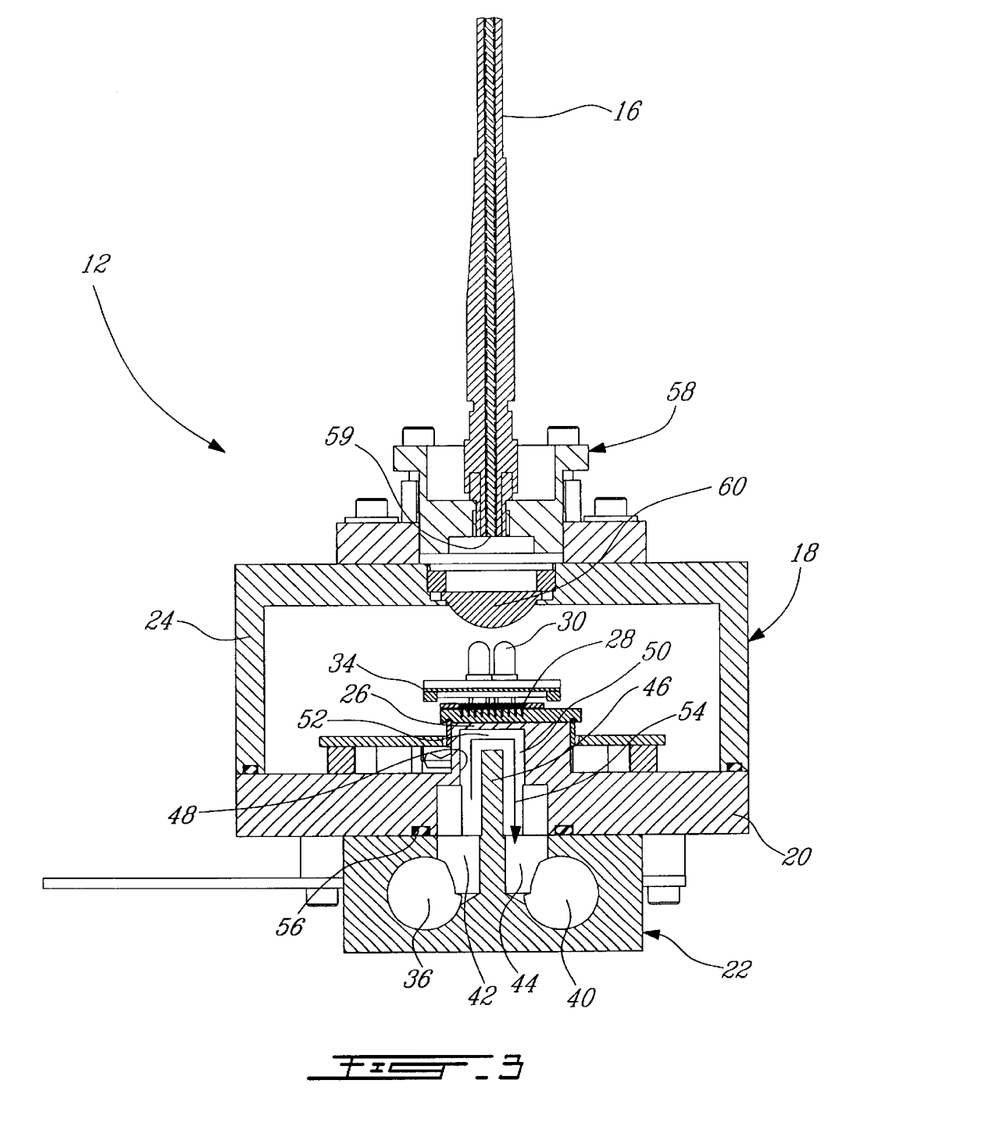
FIG. 3 is a sectional view taken along line 3—3 of FIG. 2.

Turning now to FIGS. 2 and 3 of the appended drawings, the injection module 12 will be described in greater details. The injection module 12 includes a body 18 defined by a base 20, having a cooling block 22, and by a cover 24.

The base 20 includes a heat sink base 26 to which are mounted a first radiation source, in the form of a laser diode array 28, emitting laser light. A second radiation source, in the form of four Light Emitting Diodes (LEDs) 30 (only two shown in FIGS. 2 and 4), emitting aiming beam forming light, in this case, non-coherent light, is mounted to a circuit board secured to the heat sink base 26. Two orthogonal collimating micro-lens arrays 32 and 34 is also mounted to the heat sink base 26, for example by an adhesive, to collimate the emitted laser light as will be described hereinbelow.

While the laser diode array 28 will not be described herein in detail since laser diode arrays are believed well known to those skilled in the art, adequate laser diode arrays are described in U.S. Pat. Nos. 5,040,187; 5,128,951; 5,284,790 and 5,311,535, all naming A. Karpinski as inventor, the disclosures of these documents are incorporated herein by reference. Similarly, adequate collimating micro-lens arrays are described in U.S. Pat. Nos. 5,607,492 and 5,638,214; the use of the micro-lens arrays with a laser diode array is described in U.S. Pat. No. 5,825,803, the disclosure of which are incorporated herein by reference. Micro-lens array holders are described in U.S. Pat. Nos. 5,526,373 and 5,668,825, the disclosure of which are also incorporated herein by reference.

As can be better seen from FIG. 3, the cooling block 22 includes a fluid inlet 36 to which a fluid conduit 38 (FIG. 2) may be connected and a fluid outlet 40 to which a fluid conduit (not shown) may be connected. The cooling block 22 also includes two channels 42 and 44 separated by a wall 46 extending in a channel 48 of the base 20, thereby defining an inverted U-shaped cooling channel 50 having a transversal portion 52 in the proximity of the laser diode array 28 to thereby cool the laser diode array 28 efficiently. The cooling fluid may then flow from the inlet 36 to the outlet 40 via the channel 50 (see arrow 54).

Of course, sealing features, such as for example O-ring 56, are used to prevent leaks of the cooling fluid, which may be, for example, water.

The cover 24 includes an optic fibre securing assembly 58 so positioned as to align the proximate end 59 of the fibre 16 with the optical axis of a focusing lens 60. The focusing lens 60 is used to focus the collimated laser light and the aiming beam forming light into the core of the optic fibre 16 in such a manner that the coherent light propagates through the core of the optic fibre and the aiming beam forming light propagates through the cladding.

The focusing lens 60 defining, with the micro-lens arrays 32 and 34, a lens arrangement used to collimate and focus the laser light into the core of the optic fibre and to establish the propagation of the aiming beam forming light into the cladding of the optic fibre.

Example of Elements Adequate for the Injection Module
Laser diode array: Coherent, p/n 0168-833-15
Collimating micro-lens array: Custom piano-convex and GRIN cylindrical micro-lens
DEL: Gilway, MegaBright Green, p/n E902
Focusing lens: Melles-Griot, p/n 01 LAG001/076
Optic fibre: 3M, Hard Clad, p/n FT-1.5-UMT It is to be noted that many features of the injection module 12 have not been described in detail hereinabove since they are not particularly relevant to the present invention and/or are believed well known to one skilled in the art.

Figure 4:
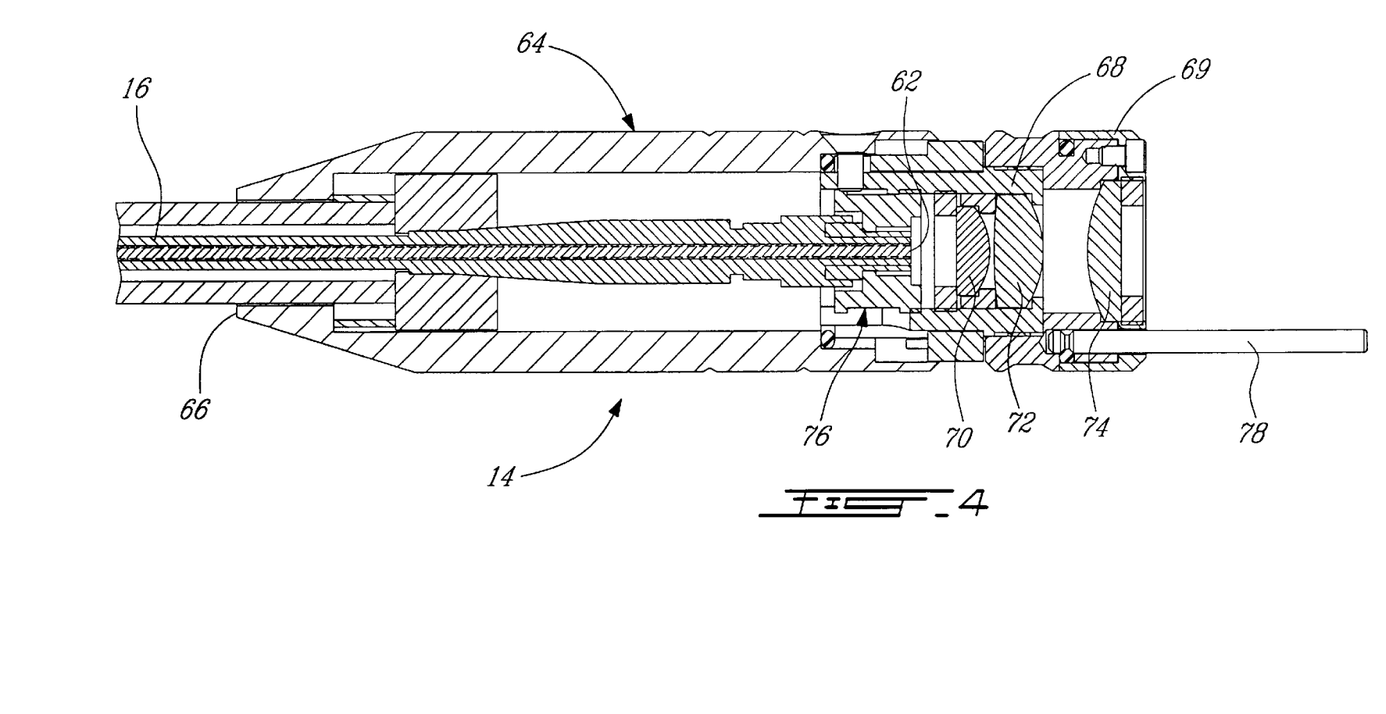
FIG. 4 is a side elevational sectional view of the handheld module of the apparatus of FIG. 1.

Turning now to FIG. 4 of the appended drawings, the handheld module 14 will be described. Generally stated, the purpose of the handheld module 14 is to reproduce the distal end 62 light output distribution of the optic fibre 16 with a predetermined magnification factor applied thereto.

The handheld module 14 includes a generally tubular body 64 having an open proximate end 66 allowing the optic fibre 16 therethrough, and a lens supporting portion 68 provided with optical elements 70 and 72. The module 14 also includes a removable focusing tube 69 to which is mounted a third lens 74, selected and positioned to apply the predetermined magnification factor to the image of the distal end 62 of the fibre 16. The optical elements 70, 72 and 74 thereby defining a lens arrangement.

For example, the optical element 70 could be a lens manufactured by Melles Griot under number 01 LPX0111/076; the optical element 72 could be a lens manufactured by ESCO Products under number ZA611220C; and the optical element 74 could be a lens manufactured by Melles Griot under number 01 LPX057/076.

Of course, the handheld module 14 also includes an optic fibre securing assembly 76 so positioned as to align the distal end 62 of the fibre 16 with the optical axis of the lens 70, 72 and 74.

The removable focusing tube 69 also includes a distance guide 78 that indicates the correct distance to be maintained between the skin of the patient and the distal end 68 of the handheld module 14 to obtain the predetermined enlargement factor.

It is to be noted that the handheld module 14, with the removable focusing tube 69, is designed to provide an enlargement factor of about 3.3333. Indeed, the 1.5 mm diameter of the end of the fibre 16 is enlarged to a 5 mm diameter aiming beam at the end of the guide 78.

Figure 5:
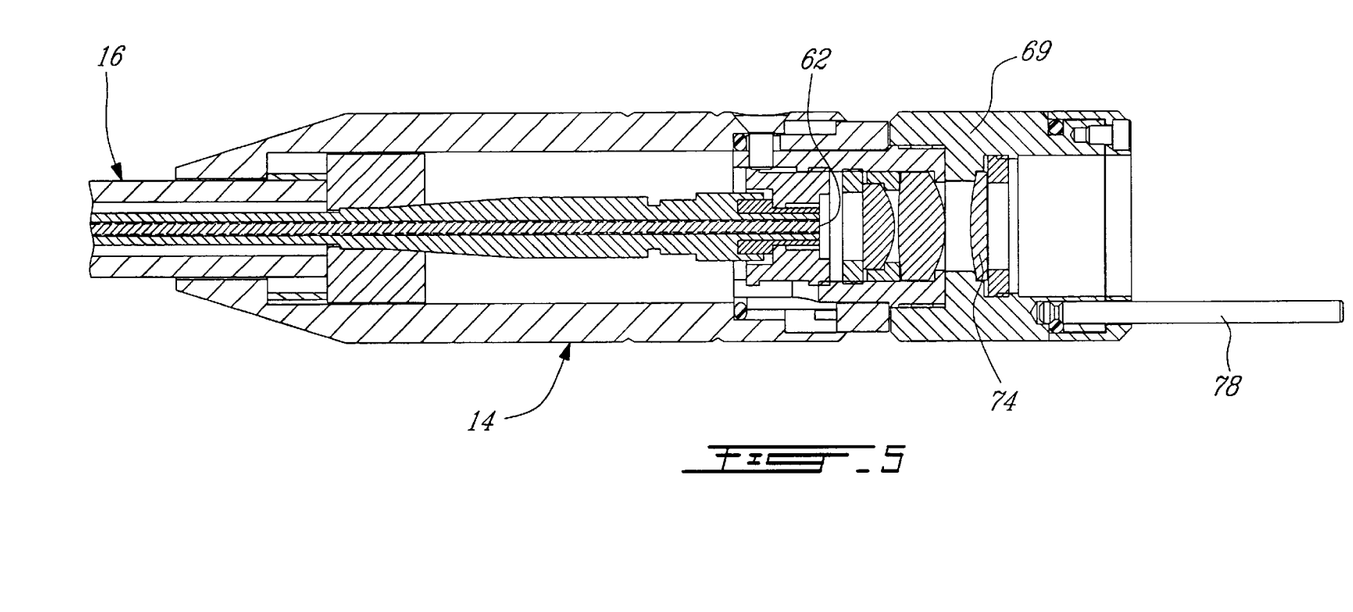
FIG. 5 is a side elevational sectional view of a handheld module similar to the module of FIG. 4 but provided with an alternate focusing tube.

Turning briefly to FIG. 5 of the appended drawings, a handheld module 14' according to an alternate embodiment will be described. It is to be noted that the handheld module 14' is very similar to the handheld module 14 described hereinabove. Accordingly, only the differences between these modules will be described hereinbelow.

The difference between the module 14' and the module 14 of FIG. 4 is that the optical elements 74' is so selected and positioned by the removable focusing tube 69' that a magnification factor of 4,667 is obtained. Indeed, the 1.5 mm diameter image of the distal end 62 of the fibre 16 is enlarged to a 7 mm diameter aiming beam at the end of the guide 78'.

For example, the optical element 74' could be a lens manufactured by CVI under number PCLX-12.7-25.8-C-800.

Figure 6:
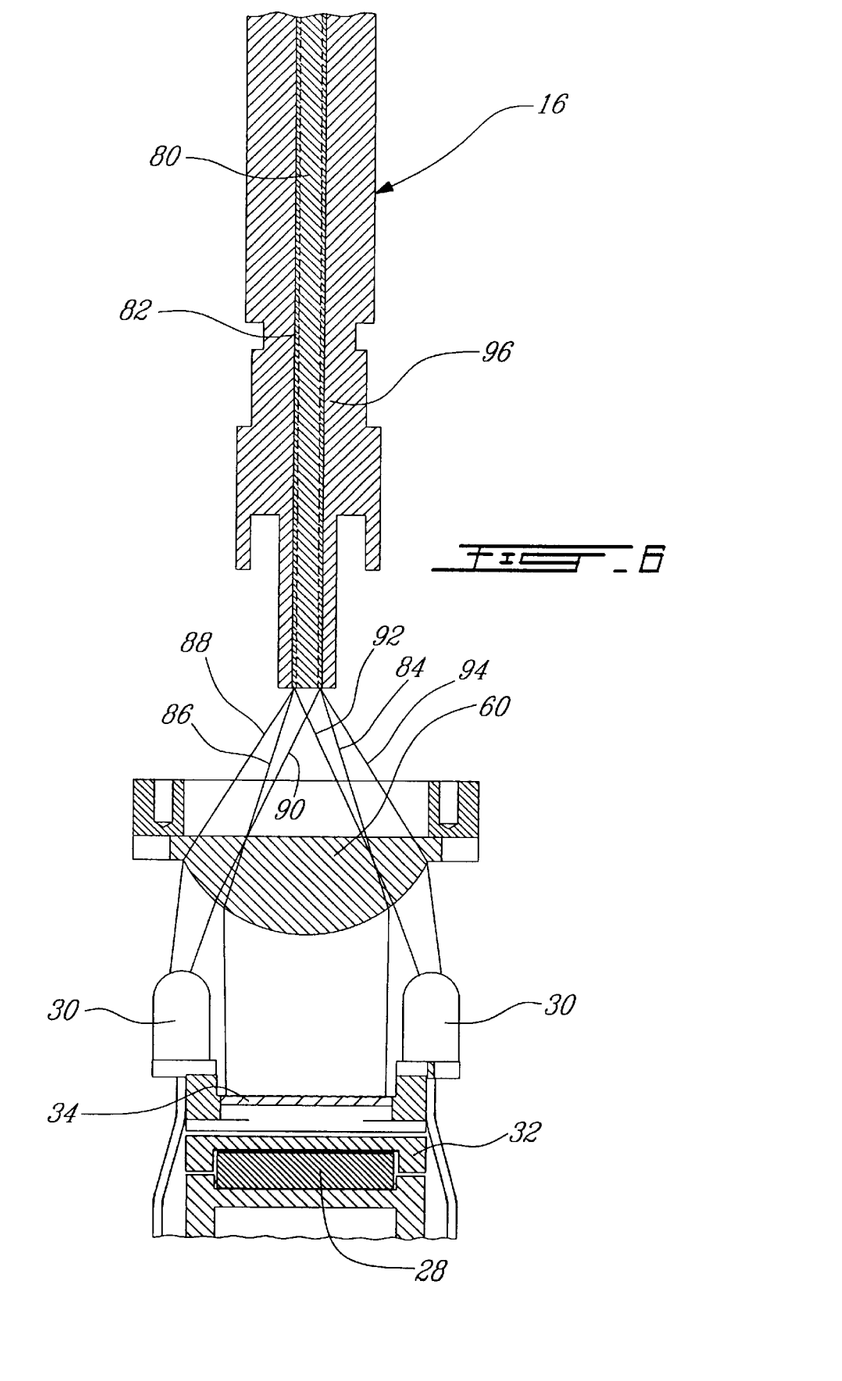
FIG. 6 is a side elevational view of a portion of the injection module of FIG. 2, illustrating the injection of the laser light and of the aiming beam forming light into the optic fibre.
Figure 7:
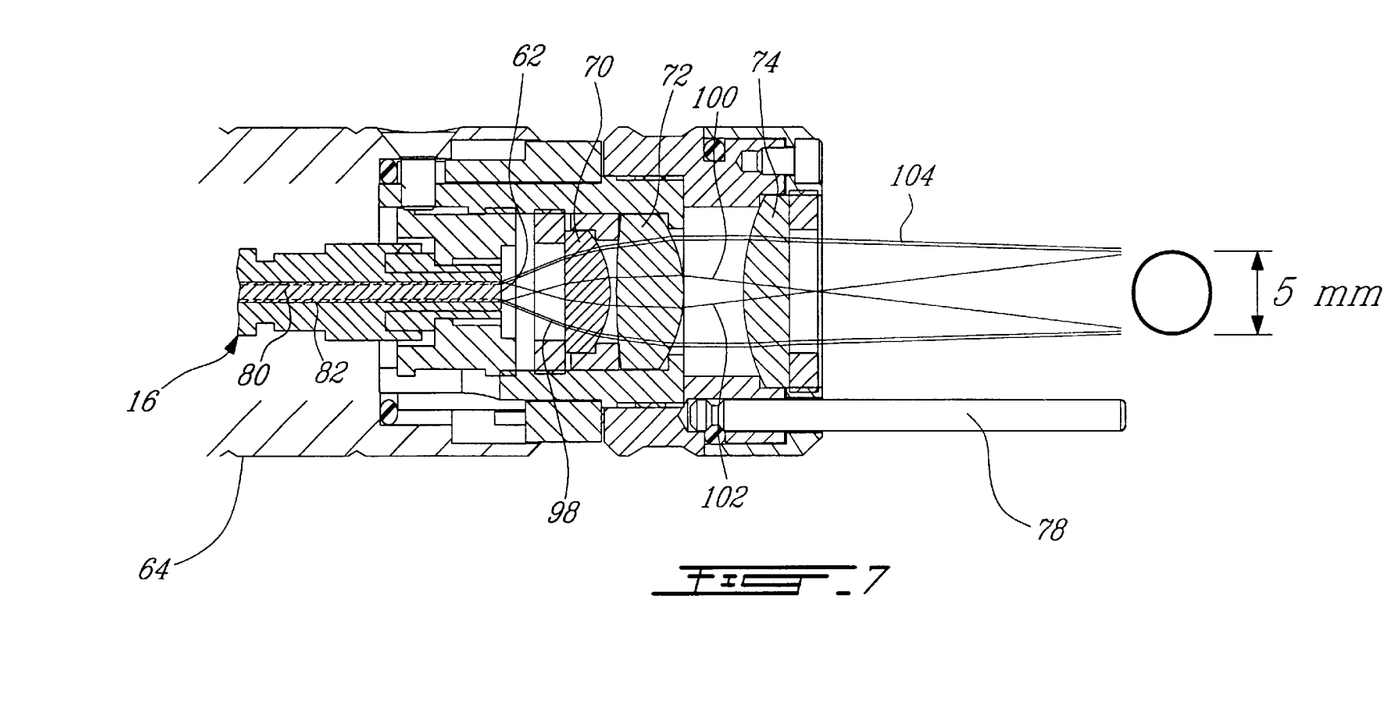
FIG. 7 is a sectional view of a portion of the handheld module of FIG. 4, illustrating the exit of the aiming beam forming light from the optic fibre.

Turning now more specifically to FIGS. 6 and 7, the injection and the exit (output) of the laser and aiming beam forming light into and out of the optic fibre 16 will be described in greater detail.

The laser light emitted by the laser diode array 28 is first collimated by the collimating micro-lens arrays 32 and 34 before being focused by the lens 60. As far as the collimated laser light is concerned, the purpose of the focusing lens 60 is to focus the light into the core 80 of the optic fibre 16 with the correct angle to ensure that the laser light is "guided" in the core 80 of the fibre 16.

As will easily be understood by one skilled in the art, the fibre optic manufactured by the 3M Company under number FT-1.5-UMT, used in the present embodiment, has a Numerical Aperture (NA) of 0.39, thereby allowing laser light to enter at a maximal angle of about 23 degrees (see schematic light lines 84 and 86), calculated from the longitudinal axis of the fibre, and still be "guided" in the core 80 of the optic fibre 16. The focusing lens 60 is therefore chosen to supply the collimated laser light to the optical fibre 16 at an angle equal of less than 23 degrees.

Regarding the non-coherent light emitted by the LEDs 30 and 32, which will become the aiming beam, it is supplied to the optic fibre 16 at an angle that is more than 23 degrees (see schematic non-coherent light lines 88, 90, 92 and 94). Since the angle of insertion of the non-coherent light is greater than 23 degrees, the internal reflection in the core 80 of the fibre 16 does not take place, leaving the non-coherent light to be guided in the cladding 82, between the core 80 and the cover 96 of the fibre 16.

Turning now briefly to FIG. 7 of the appended drawings, the exit of the aiming beam forming light from the optic fibre 16 will be described. As can be seen from the schematic non-coherent light lines 98, 100, 102 and 104 of this figure, the light emerging from the cladding 82 of the fibre 16 at the distal end 62 thereof is refracted by the lenses 70, 72 and 74 to obtain the predetermined diameter of the aiming beam at the end of the guide 78. As discussed hereinabove with reference to FIG. 4, the predetermined diameter of the circular aiming beam light exiting the cladding of the fibre 16 is 5 mm, in this case.

One skilled in the art will appreciate that since the aiming beam is transmitted in the cladding 82 of the fibre 16, the position of the aiming beam surrounding the laser light is always maintained.

It is to be noted that it has been found advantageous to use green color LEDs to improve the visibility of the positioning spot with most conventional laser eye protection. Indeed, the high power laser diode of the present invention emits in the near infrared spectrum. Laser protection goggles provide absorption in the near infrared spectrum. The laser protection goggles therefore offer good transmission and excellent visibility of the green light emitted by the LEDs.

As will easily be understood by one skilled in the art, the green colored LED could be replaced by other light emitting devices. For example, low power laser diodes could be used without departing from the spirit and nature of the present invention.

Another advantage of the apparatus 10 is the use of a single optic fibre 16 that allows much simpler and reliable connection and alignment to deliver very high Infrared (IR) laser energy from the fibre to the handheld module. Moreover, it allows an extended flexibility and easier manipulation of the handheld module 14.

It is to be noted that while the laser diode apparatus 10 is designed for hair removal, the injection techniques used in this apparatus to provide an aiming beam surrounding laser light could easily be used for other purposes such as, for example, Dermatology/Plastic surgery treatment (Hair removal, Vascular lesions, Benign Pigmented lesions, Dermal Remodeling, Exophytic lesions of the skin, etc), endoscopic laser surgery such as: any Gastro-enterologic lesions (angiodysplasia, polyps, vascular lesions, etc.) that could be vaporized with high power laser energy. Indeed, the aiming beam would help the operator aiming the laser energy to the correct location. The laser diode apparatus 10 could also be used for any Cardiovascular lesions i.e., coronary thrombus, etc., any Oto-rhino-laryngologic benign and neoplastic lesions, any Obstetric and Gynecology benign and neoplastic lesions and pulmonary benign and neoplastic lesions that could be vaporized with high power laser energy. Laser tissue welding could also be performed with the help of the laser diode apparatus of the present invention providing the ideal parameters for such an application.

It is also to be noted that while only medical uses have been described hereinabove, industrial uses of the above described technology may be envisioned. For example, laser metal soldering systems could be designed with the aiming beam as described herein.

Although the present invention has been described hereinabove by way of preferred embodiments thereof, it can be modified, without departing from the spirit and nature of the subject invention as defined in the appended claims.

What is claimed is:

1. An injection module for injecting laser light and aiming beam forming light into an optic fibre having a core and a cladding; said injection module comprising:
    a first radiation source emitting laser light;
    a second radiation source emitting aiming beam forming light; wherein said second radiation source emits non-coherent light; and
    a lens arrangement so configured as to a) collimate and focus the emitted laser light into the core of the optic fibre, and b) establish the propagation of the aiming beam forming light into the cladding of the optic fibre.

2. An injection module as recited in claim 1, wherein said second radiation source emits non-coherent light.

3. An injection module as recited in claim 2, wherein said second radiation source includes at least one Light Emitting Diode (LED) emitting non-coherent light.

4. An injection module as recited in claim 3, wherein said at least one LED includes four LEDs.

5. An injection module as recited in claim 1, wherein said lens arrangement includes at least one micro-lens collimating array to collimate the laser light.

6. An injection module as recited in claim 5, wherein said at least one micro-lens array includes two orthogonal collimating micro-lens arrays.

7. An injection module as recited in claim 5, wherein said lens arrangement further includes a focusing lens so configured and positioned as to focus said collimated laser light in the core of the optic fibre and to ensure the propagation of the aiming beam forming light into the cladding of the optic fibre.

8. An injection module as recited in claim 1, further including a base provided with a cooling block, and wherein said first radiation source emitting laser light is mounted in the vicinity of said cooling block to be cooled thereby.

9. An injection module as recited in claim 8, further comprising a cover mountable to said base and including an optic fibre securing assembly.

10. A laser diode apparatus comprising:
    an optic fibre having a core and a cladding; said optic fibre having a proximate and a distal end;
    an injection module for injecting laser light and aiming beam forming light into said proximate end of said optic fibre; said injection module including:
      a first radiation source emitting laser light;
      a second radiation source emitting aiming beam forming light; and
      a lens arrangement so configured as to a) collimate and focus the emitted laser light into the core of the optic fibre, and b) establish the propagation of the aiming beam forming light into the cladding of the optic fibre; and
    a handheld module mounted to said distal end of said optic fibre.

11. A laser diode apparatus as recited in claim 10, wherein said second radiation source emits non-coherent light.

12. A laser diode apparatus as recited in claim 11, wherein said second radiation source includes at least one Light Emitting Diode (LED) emitting non-coherent light.

13. A laser diode apparatus as recited in claim 12, wherein said at least one LED includes four LEDs.

14. A laser diode apparatus as recited in claim 10, wherein said lens arrangement includes at least one micro-lens collimating array to collimate the laser light.

15. A laser diode apparatus as recited in claim 14, wherein said at least one micro-lens array includes two orthogonal collimating micro-lens arrays.

16. A laser diode apparatus as recited in claim 14, wherein said lens arrangement further includes a focusing lens so configured and positioned as to focus said collimated laser light in said core of said optic fibre and to establish the propagation of the aiming beam forming light into the cladding of said optic fibre.

17. A laser diode apparatus as recited in claim 10, wherein said injection module further includes a base provided with a cooling block, and wherein said first radiation source emitting laser light is mounted in the vicinity of said cooling block to be cooled thereby.

18. A laser diode apparatus as recited in claim 17, wherein said injection module further includes a cover mountable to said base and including an optic fibre securing assembly.

19. A laser diode apparatus as recited in claim 10, wherein said handheld module includes a lens arrangement configured and positioned to reproduce a light output distribution of said distal end of said optic fibre with a predetermined magnification factor.

20. A method for injecting laser light and aiming beam forming light into an optic fibre having a core and a cladding; said method comprising the steps of:
  providing a source of laser light;
  providing a source of aiming beam forming light;
  collimating and focusing the laser light emitted by the source of laser light into the core of the optic fibre; and
  establishing the propagation of the aiming beam forming light emitted by the source of aiming beam forming light into the cladding of the optic fibre.

* * * * *